United States Patent [19]
Butler et al.

[11] Patent Number: 5,749,381
[45] Date of Patent: May 12, 1998

[54] TOOTHBRUSH FOR IMPLEMENTING THE BASS BRUSHING TECHNIQUE

[76] Inventors: C. P. Butler, 4615 Shumart Dr., Lithonia, Ga. 30058; F. M. Butler, Jr., 3118 SW. 20th Ter., Del Ray Beach, Fla. 33445

[21] Appl. No.: 622,697

[22] Filed: Mar. 26, 1996

Related U.S. Application Data

[60] Provisional application No. 60/011,896 Feb. 20, 1996.

[51] Int. Cl.$^6$ .............................. A45D 44/18; A45D 8/18; A46B 9/04
[52] U.S. Cl. .......................... 132/309; 132/323; 15/167.1; 15/143.1
[58] Field of Search ........................... 132/308, 309, 132/310, 321, 323, 324, 325, 326, 327, 328, 329; 15/167.1, 143.1

[56] References Cited

U.S. PATENT DOCUMENTS

| | | | |
|---|---|---|---|
| 2,962,033 | 11/1960 | Lew | 132/324 |
| 4,227,276 | 10/1980 | Ginsburg et al. | 15/176 |
| 4,454,623 | 6/1984 | O'Halloran. | |
| 4,471,504 | 9/1984 | Anderson | 15/23 |
| 4,508,125 | 4/1985 | Loubier | 132/326 |
| 4,598,437 | 7/1986 | Ernest et al. | 15/167.1 |
| 4,829,621 | 5/1989 | Phenegar | 15/167.1 |
| 4,875,248 | 10/1989 | Kent | 15/167.1 |
| 5,027,463 | 7/1991 | Daub | 15/22.1 |
| 5,040,261 | 8/1991 | Kirberger | 15/167.1 |
| 5,095,924 | 3/1992 | Stanfield | 132/310 |
| 5,127,415 | 7/1992 | Preciutti | 132/308 |
| 5,305,489 | 4/1994 | Lage | 15/167.1 |
| 5,305,490 | 4/1994 | Lundgren | 15/167.1 |
| 5,305,491 | 4/1994 | Hegemann | 15/167.2 |
| 5,406,965 | 4/1995 | Levine | 132/323 |
| 5,499,422 | 3/1996 | Lavazoli | 15/167.1 |

FOREIGN PATENT DOCUMENTS

| | | | |
|---|---|---|---|
| 0274618 | 7/1988 | European Pat. Off. | 15/167.1 |
| 2702636 | 9/1994 | France | 15/167.1 |
| 6165712 | 6/1994 | Japan | 15/167.1 |

*Primary Examiner*—Cary E. O'Connor
*Attorney, Agent, or Firm*—Deveau, Colton & Marquis

[57] ABSTRACT

An ergonomically designed toothbrush having an oversized handle, a shapeable stem, interchangeable heads of different sizes, bristle arrangements, and geometrical configurations. The handle is generally cylindrical in shape so as to readily fit in the palm of one's hand while having a flattened portion against which the thumb and fingertips may be rested. The stem is attached to the handle in such a manner as to allow rotation of the stem in a variety of positions about the longitudinal axis of the handle. The use of the toothbrush may set the orientation of the bristles on the heads such that they are at a 45° inclination relative to the surface of the teeth while the flat portion of the handle is generally parallel to the surface of the teeth so that the Bass technique may be implemented white moving the toothbrush back and forth in short strokes in a conventional manner.

16 Claims, 4 Drawing Sheets

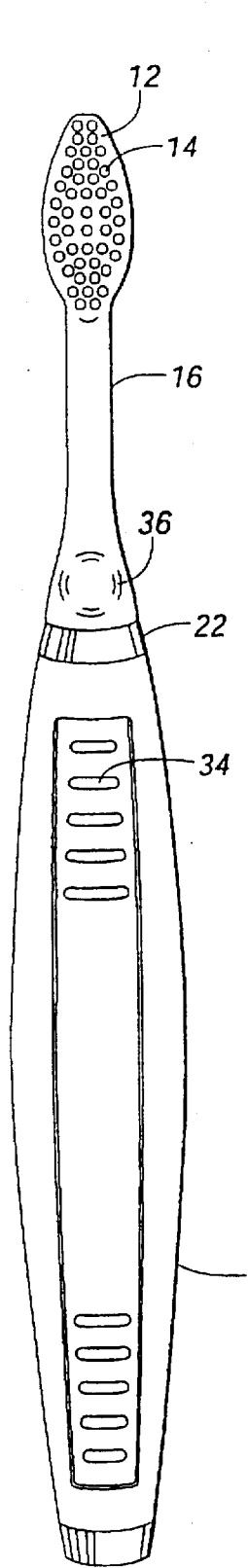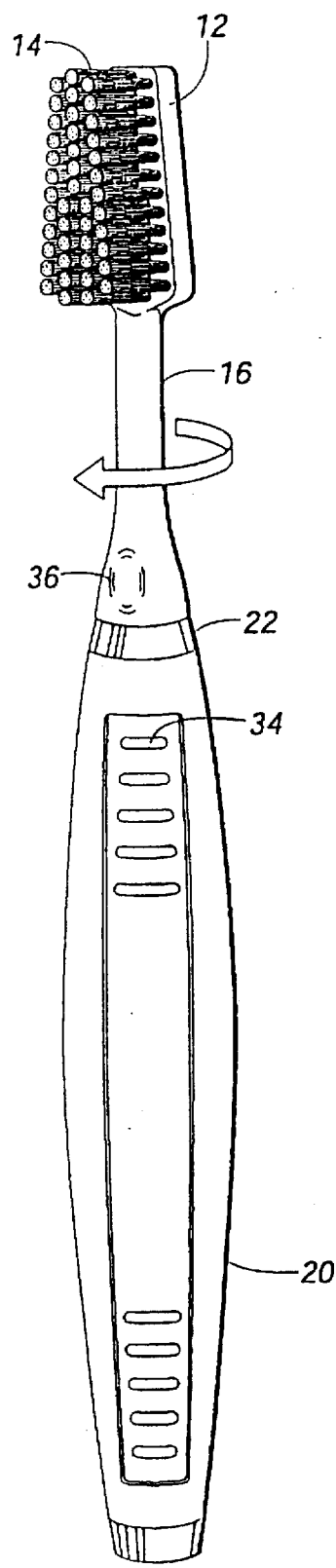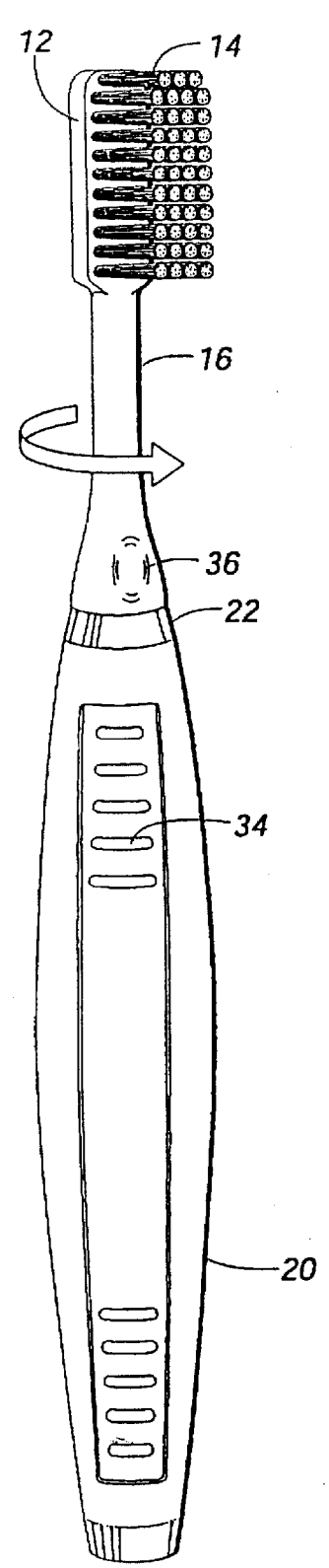
FIG. 2a  FIG. 2b  FIG. 2c

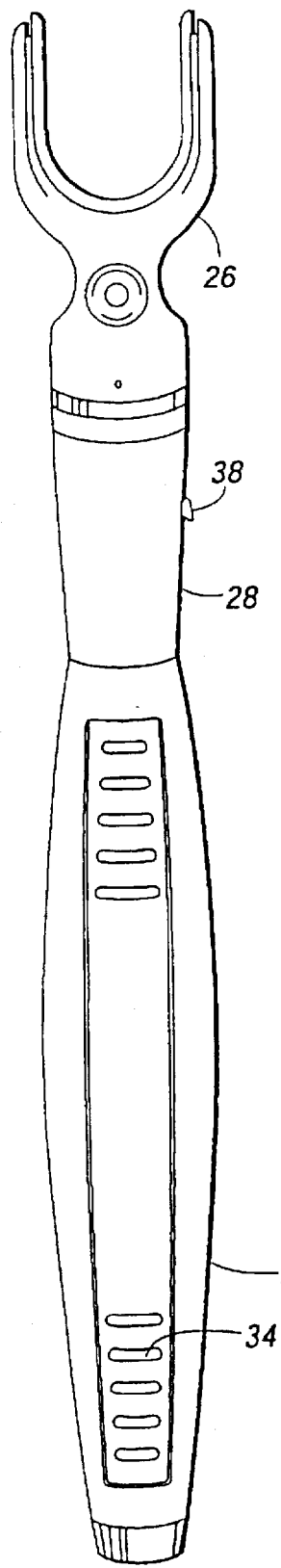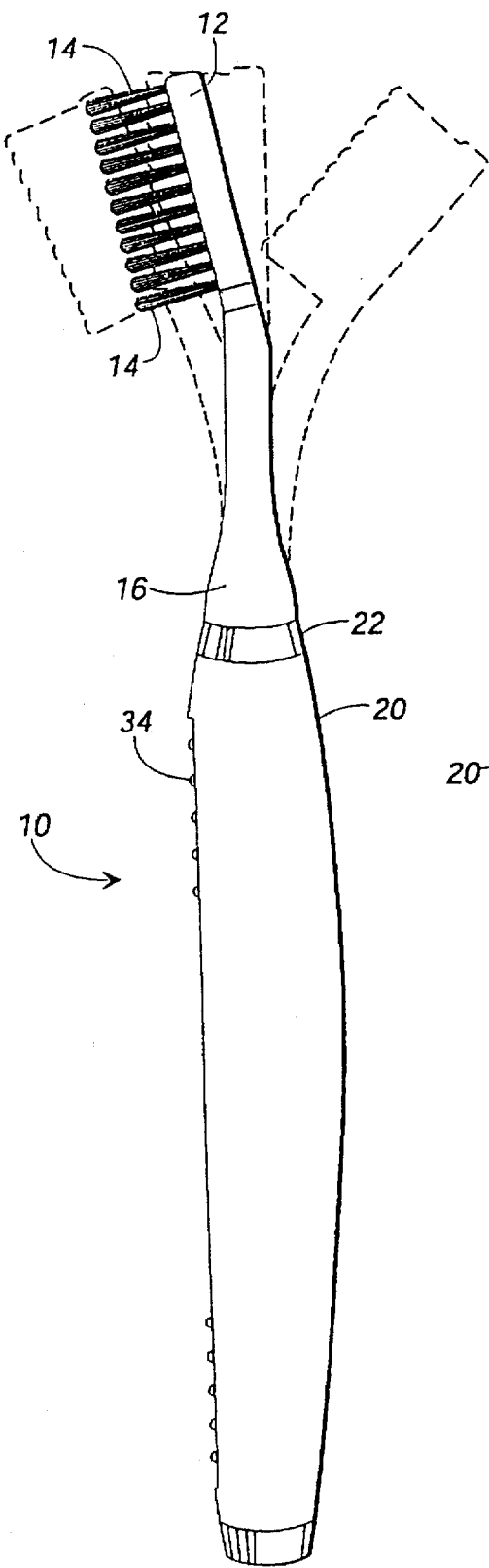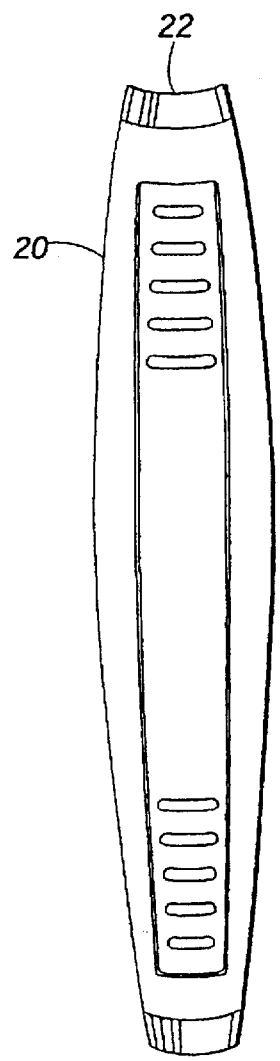
*FIG. 2d*   *FIG. 3*   *FIG. 4*

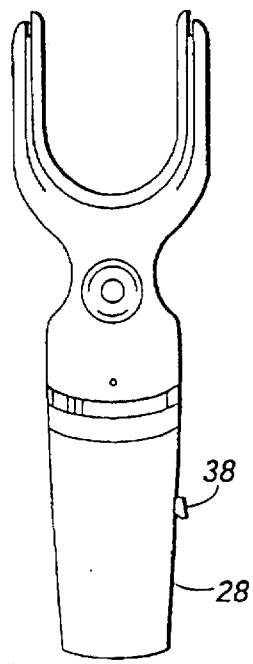 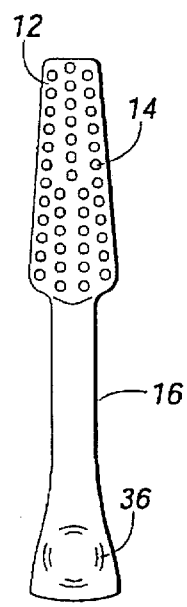 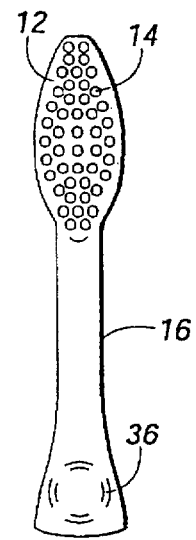 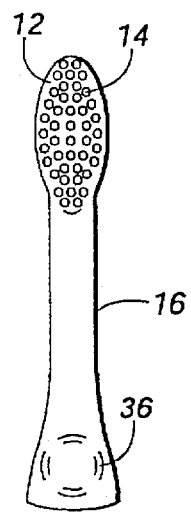
FIG. 5a  FIG. 5b  FIG. 5c  FIG. 5d
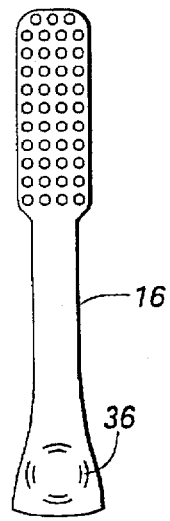
FIG. 5e

5,749,381

TOOTHBRUSH FOR IMPLEMENTING THE BASS BRUSHING TECHNIQUE

This application claims the benefit of U.S. provisional applications Ser. No. 60/011,896 filed of Feb. 20, 1996.

BACKGROUND OF THE INVENTION

1. Field of the Invention

This invention relates generally to toothbrushes and more particularly is directed to a toothbrush with interchangeable heads which may be rotated about the axis of the handle so that the head of the toothbrush is positioned at an optimum angle relative to the surface of the teeth and gums.

2. Description of the Prior Art

The Bass technique of brushing teeth is widely recommended by the American Dental Association for removal of plaque which accumulates on the surface of the teeth and in the sulcus, i.e., the tooth surface which is hidden by the gums. Basically, this technique involves holding a standard toothbrush at about a 45° angle relative to the surface of the teeth such that a portion of the bristles clean the teeth while another portion of the bristles clean the gums as the toothbrush is moved back and forth in short strokes. Implementation of this technique with a standard toothbrush requires that the user of the toothbrush rotate his or her wrist at about a 45° angle while at the same time using the short back and forth strokes required by the Bass technique on both the front and back surfaces of the teeth, both the top and bottom sets. Holding ones wrist in this unnatural position while brushing for the time period recommended by dental professionals can be quite tiring particularly for children and individuals with arthritis. Often these individuals do not have the necessary manual dexterity or stamina to effectively practice the Bass brushing technique. Therefore, a need exists for a toothbrush which facilitates use of the Bass brushing technique while not imposing unnecessary burdens on the user of the toothbrush such as hand and wrist fatigue which discourage proper brushing technique and encourage reversion to less effective brushing techniques. Thus, there is a need for a toothbrush which allows one to easily implement the Bass brushing technique. It is to the provision of such a toothbrush that the present invention is primarily directed.

Another short coming of standard toothbrushes relates to failure of the toothbrush user to follow dental professionals'recommendation that the toothbrush bristles be completely dried between uses. This recommendation is at odds with the recommendation that brushing take place after each meal, particularly if only one toothbrush is used. For example, if one eats breakfast at about eight o'clock and brushes his or her teeth thereafter, it is unlikely that the toothbrush bristles will be dry by one o'clock or so after he or she has had lunch unless the toothbrush is stored at an elevated temperature or a specific drying means is utilized. Thus, there is a need for a system of oral hygiene which permits one to utilize a toothbrush wherein the bristles are dried between subsequent uses.

BRIEF SUMMARY OF THE INVENTION

The present invention is a toothbrush for easily implementing the Bass brushing technique. The toothbrush has a generally cylindrical handle which is oversized to enhance manual dexterity and to make gripping of the handle more comfortable for the user. The generally cylindrical handle has a flattened portion along its length against which the thumb and fingertips may be rested so as to firmly hold the handle at a fixed angle while brushing. Connected to the handle is a rotation means to which a variety of interchangeable stems may be connected, all of which have a head of a different size, bristle arrangement, or geometrical configuration. The rotation means is adapted so that it may be selectively positioned at one of a plurality of locations about the longitudinal axis of the handle. With such an arrangement, the Bass brushing technique may be implemented by attaching a stem with a preferred head shape to the rotation means and adjusting the rotation means so that the bristles are aligned at a 45° angle relative to the surface of the teeth while the flat portion of the handle is generally parallel to the surface of the teeth. A significant achievement of the present invention is provided by multiple raised sections or grips on both the flat portion and the generally cylindrical portions of the handle which permit the user of the toothbrush to brush all dental surfaces while maintaining the same grip on the handle and simply adjusting the rotational angle of the head.

Optionally, the head connected to the stem may be replaced with a dental floss holding device for storing dental floss and for mounting a length of dental floss thereon allowing one to floss the areas between teeth. Also, the handle of the toothbrush may be formed of a rubberized material which is slightly depressed when force is applied thereto so as to reduce hand and wrist fatigue when brushing. A ventilated storage container for drying toothbrush bristles in a protected environment may also be provided.

Thus, it is an object of the present invention to provide a toothbrush having a construction which facilitates implementation of the Bass brushing technique.

It is another object of the present invention to provide a toothbrush having interchangeable heads so that heads having a variety of sizes, shapes, bristle arrangements and geometrical configurations may be used.

It is another object of the present invention to provide a toothbrush which may be converted for use as a device for flossing.

It is yet another object of the present invention to provide a toothbrush having a handle which is ergonomically designed to reduce wrist and hand fatigue while brushing.

Yet another object of the present invention is to provide an oral hygiene system allowing for interchangeable toothbrush heads of different configurations which, when used over a period of time, insure that all surfaces of the teeth are cleaned during brushing.

Still another object of the present invention is to provide an oral hygiene system which allows for adequate drying of toothbrush bristles between subsequent uses.

A further object of the present invention is to provide a complete oral care system that includes means for flossing teeth.

These objects, and other objects, features and advantages of the present invention will become more apparent to one skilled in the art when the following detailed description of the preferred embodiment is read in conjunction with the appended drawings in which like reference numerals designate like parts throughout the several views.

BRIEF DESCRIPTION OF THE DRAWINGS

FIGS. 2a is a front view of the toothbrush of the present invention demonstrating a standard head orientation.

FIGS. 2b–2c are front views of the toothbrush of FIG. 2a showing the head rotated 45 degrees from the position depicted in FIG. 2a.

FIG. 2d is a front view of the toothbrush of FIG. 2a with the head replaced with a preferred embodiment of the dental floss holder of the present invention.

FIG. 3 is a side view of the toothbrush of FIG. 2a demonstrating various static positions in which the stem may be placed.

FIG. 4 is a front view of the handle of the toothbrush depicted in FIG. 2a.

FIGS. 5a–5e are front views of preferred attachments for the toothbrush handle depicted in FIG. 4.

DETAILED DESCRIPTION OF THE PREFERRED EMBODIMENTS

Figure 1:
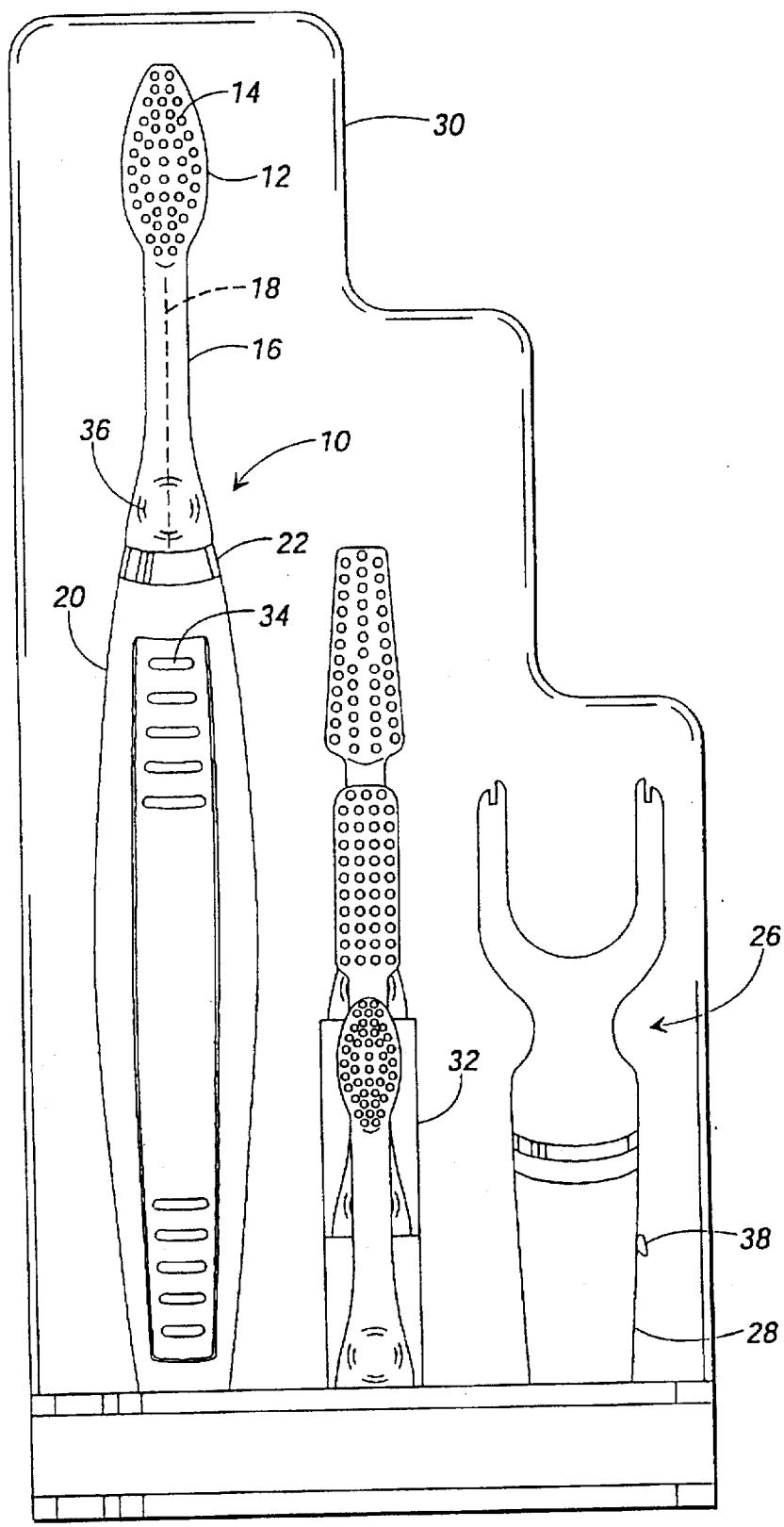
FIG. 1 is a front view of the oral hygiene system of the present invention including toothbrush handle, interchangeable heads, dental floss holder, and a preferred storage and drying container.

The present invention is a toothbrush for implementing the method of brushing teeth which is recommended by the American Dental Association (ADA), i.e., the Bass brushing technique. This technique has been shown to be most effective in removing plaque and food particles from the inner, outer, and biting surfaces of teeth as well as the gingival margin. The technique involves holding a toothbrush at approximately a forty-five (45) degree angle relative to the surface of the teeth with about half the bristles touching the teeth and the other half touching the gums while gently moving the toothbrush back and forth in short (half-a-tooth-wide) strokes.

Referring now to the drawings, FIG. 1 shows the complete oral care system of the present invention mounted in a transparent storage container 30 having a plurality of apertures (not shown) therein for ventilation. The storage container 30 provides a convenient means of drying toothbrush bristles and guards against bacterial contamination which frequently occurs when a toothbrush is simply placed on a countertop. The base of the storage container 30 may be provided with appropriately shaped notches (not shown) and shelves 32 to accommodate the bottom portions of the various components of the oral care system.

The oral care system includes a padded handle 20 which has a larger diameter than the standard, commercially available toothbrush which makes the handle 20 more comfortable and easier to use because less force is required to stably hold the handle 20. Also, the larger handle 20 requires less rotational turning about the longitudinal axis of the handle 20 than is required by a smaller handle to achieve the same result. The handle 20 is generally cylindrical in shape having a cross section which is predominantly circular (about one inch in diameter) except for a generally flat portion defined by a chord of the circular cross section of the handle. As better shown in FIG. 3, the generally flat portion extends along almost the entire length of the handle 20 and provides a convenient surface against which one's thumb and fingertips may be placed while brushing. The handle 20 is preferably formed of a "squeezable" material which deflects slightly when a gripping force is applied. Such a construction makes the toothbrush 10 more comfortable to hold and therefore easier to use. Optionally, the toothbrush of the present invention may be formed with a flat portion and grips on both the front and back (not shown) of the handle to aid in more firmly grasping the handle, particularly when the handle is wet. In the "double-sided" configuration one is enabled to implement the Bass brushing technique in all quadrants of the mouth while maintaining the same grip on the handle. The grips 34 may be arranged either vertically or horizontally as depicted in FIG. 3. The provision of multiple raised sections or grips 34 on both the front and back of the handle 20 permit the user of the toothbrush 10 to brush all dental surfaces while maintaining the same grip on the handle 20 by simply adjusting the rotational angle of the head 12 to a 45 degree angle relative to the surface of the teeth and gums.

Attached to the top portion of the handle 10 is a rotating disk 22 which is designed to detachably receive various attachments having teeth cleaning implements such as a toothbrush head or dental floss holder formed at the end of a support stem. The rotating disk preferably has a fixed portion which is secured to the handle 20 and a rotating portion designed to be turned 360 degrees in either a clockwise or counterclockwise direction so that in one position, a stem 16 may be placed in the rotating disk so that the plane defined by the tips of the tufts of bristles 14 on the head 12 is generally parallel to the flat portion of the handle. In the preferred embodiment, the head 12 may be rotated in 45 degree increments. However, it will be clear to those skilled in the art that other angular increments may be utilized while still permitting implementation of the Bass brushing technique. For example, 1 degree or 15 degree increments may be used. With such an arrangement, the toothbrush head 12 can easily be used to carry out the Bass brushing technique by rotating the head 12 so that the bristles 14 are at about a 45 degree angle relative to the surface of the teeth.

As shown in FIG. 3, the stem 16 of the toothbrush 10 of the present invention is bendable so that the stem 16 and head 12 can be positioned at any fixed position necessary to reach areas of the mouth which are otherwise difficult to reach with a standard toothbrush. To achieve this purpose, the stem 16 may be provided with a centrally located wire 18 of a size and stiffness sufficient to maintain the head 12 and stem 16 configuration selected by the user of the toothbrush 10 while at the same time withstanding the forces applied to the head and stem during brushing. The stem 16 is connected to the handle 20 by snapping the stem 16 in place on the rotating disk 22 preferably with small flexible projections on the bottom of the stem extending through appropriately sized apertures formed in the rotating portion of the rotating disk 22. One or more circular indentations 36 are provided at the base of each stem 16 to assist in gripping the stem when it is being connected to the handle 20 via the rotating disk 22.

As shown in FIGS. 5b–5e, the toothbrush 10 of the present invention includes a plurality of detachable stems 16 with heads 12 of different sizes and shapes containing rows with tufts of bristles 14 variously arranged. In particular, FIG. 5c shows a large oval-shaped head, FIG. 5d shows a small oval-shaped head, FIG. 5e shows a generally rectangular head, and FIG. 5b shows a generally rectangular shaped head wherein the tip to of the head is more narrow than the base of the head in the shape of a truncated triangle. In the preferred embodiment, three of the head designs shown have soft bristles while a fourth toothbrush head has hard bristles which are especially effective for occlusals. When the features of the multiple head arrangements are combined with the flexible positioning capabilities of the stem 16, one obtains a toothbrush 10 which can be adapted to utilize practically all of the head designs and stem angles which are recommended and used by the various toothbrush manufacturers.

As shown in FIG. 5a, the present invention also includes a tubular stem 28 to which a generally U-shaped dental floss holder 26 is attached. The tubular stem 28 of the dental floss holder 26 is tubular in construction so as to accommodate a roll of dental floss therein. A dental floss cutter 38 is attached to or formed in the side of the tubular stem 28. The tubular stem 28 is attached to the handle 20 in the same maimer as described above with respect to attachment of the stems 16 which have toothbrush heads 12 with bristles 14.

Use of the toothbrush 10 of the present invention by a right-handed person will now be described. First, the stem 16 having the desired toothbrush head 12 is attached to the rotating disk 22 on top of the handle 20. For this purpose, the stem 16 may include a plurality of small projections or bars on its bottom portion which are shaped to fit into a plurality of grooves formed in the rotation means so that the stem 16 is locked in place by inserting the bars into the grooves and rotating the stem 16 until the stem is locked in place. Next the stem 16 is flexed and formed to the preferred lateral displacement relative to the flat portion of the handle. The toothbrush 10 is then moved into a horizontal position in front of the mouth with the head 12 on the left (bristles 14 facing the mouth) and the handle 20 on the right (flat portion facing mouth). The thumb should be positioned on the flat portion of the handle with the fingers curled around the stem 16. Some of the fingertips may also be positioned on the flat portion of the handle.

To brush the outside surface of the teeth in the upper left quadrant of the mouth, the stem 16 and head 12 are rotated 45 degrees upward (FIG. 2c). The toothbrush 10 is now in position to implement the Bass brushing technique by applying toothpaste to the bristles 14, placing the bristles of the toothbrush against the teeth and gums and using short back and forth strokes as described above. To brush the outside surface of the teeth in the upper right quadrant of the mouth, the same grip is maintained on the handle 20 of the toothbrush. However, the stem 16 and head 12 are rotated so that they are positioned at an upwardly inclined 45 degree angle relative to the outside surface of the teeth (FIG. 2b). When brushing these teeth, the toothbrush is still in a horizontal position in front of the mouth except that the head 12 is now on the right (bristles 14 facing the mouth) and the handle 20 on the left (flat portion facing away from the mouth). Thus, the Bass brushing technique is implemented while using conventional brushing methods without having to contort and angle the hand and wrist into an unnatural position to achieve proper positioning of the head of the toothbrush at a 45 degree angle relative to the front and back surfaces of the teeth. Of course, the dental floss holder 26 may be attached to the handle 20 and the teeth flossed in a conventional manner (FIG. 2d).

Although the present invention has been described with reference to preferred embodiments thereof, it is to be understood that these embodiments are for illustrative purposes and should not be construed as limitations on the scope of the invention. Many modifications are possible. Accordingly, the scope of the present invention should not be determined by the embodiments illustrated, but by the claims appended hereto and their legal equivalents.

We claim:

1. A toothbrush for easily implementing the Bass technique of brushing teeth and gums, comprising:
    a generally cylindrical handle, having a top portion, a central portion, a bottom portion, a longitudinal axis, and a cross-section defined by a circular portion for supporting one or more fingers and a flat portion for supporting a thumb and fingertips, wherein said handle is formed of a deformable material which is slightly depressed when a gripping force is applied thereto;
    rotation means attached to the top portion of said handle which may be selectively positioned at one of a plurality of locations about the longitudinal axis of said handle, wherein said rotation means comprises a rotating disk; and
    a stem connected to said rotation means, said stem comprising means for laterally adjusting the position of said stem relative to the longitudinal axis of said handle, said stem further comprising a head having a front portion with a plurality of tufts of bristles anchored therein, said front portion being arranged so that in one of said plurality of locations of said rotation means the bristles of the head are at about a forty-five degree angle relative to the surface of the teeth and gums when said flat portion of said handle is generally parallel to the surface of the teeth, and a bendable wire centrally located in said stem of a size and stiffness sufficient to maintain the head and stem configuration selected by the user while at the same time sustaining the forces applied to said head and stem during brushing
    whereby the Bass technique of brushing teeth and gums is implemented by the user of the toothbrush by moving the toothbrush in short strokes against the surface of the teeth in a conventional manner.

2. The toothbrush as recited in claim 1 wherein said handle has a front portion and a back portion, both having a plurality of raised sections attached thereto defining grips.

3. The toothbrush as recited in claim 2 wherein said generally cylindrical handle is about 1 inch in diameter.

4. The toothbrush as recited in claim 1 wherein said rotation means may be selectively positioned in about 45 degree increments.

5. The toothbrush as recited in claim 1 wherein said head is generally rectangular in shape.

6. The toothbrush as recited in claim 1 wherein said head is generally oval in shape.

7. The toothbrush as recited in claim 1 wherein said head is generally triangular in shape.

8. A dental flosser, comprising:
    a generally cylindrical handle having a top portion, central portion, a bottom portion, a longitudinal axis, and a cross-section defined by a circular portion for supporting one or more fingers and a flat portion for supporting a thumb and fingertips;
    rotation means attached to the top portion of said handle which may be selectively positioned at one of a plurality of locations about the longitudinal axis of said handle, wherein said rotation means comprises a rotating disk;
    a tubular stem attached to said rotation means for receiving a roll of dental floss; and
    a generally U-shaped dental floss holder attached to said tubular stem.

9. The dental flosser as recited in claim 8 wherein said tubular stem has a dental floss cutter attached thereto.

10. The dental flosser as recited in claim 8 wherein said dental floss cutter is formed integral with said tubular stem.

11. An oral hygiene system, comprising:
    a generally cylindrical handle having a top portion, a central portion, a bottom portion, a longitudinal axis, and a cross-section defined by a circular portion for supporting one or more fingers and a flat portion for a thumb and fingertips, wherein said handle is formed of a deformable material which is slightly depressed when a gripping force is applied thereto, said circular portion and said flat portion having a plurality of raised sections attached thereto defining grips;
    rotation means attached to the top portion of said handle which may be selectively positioned at one of a plurality of locations about the longitudinal axis of said handle, wherein said rotation means comprises a rotating disk;

a plurality of stems which may be detachably connected to said rotation means, said stems comprising means for laterally adjusting the position of said stems relative to the longitudinal axis of said handle, wherein each of said stems having heads of different shapes and bristles arrangements connected thereto, and said stems comprise a bendable wire centrally located in said stems of a size and stiffness sufficient to maintain the head and stem configuration selected by the user while at the same time sustaining the forces applied to the head and stem during brushing; and a dental floss holder having a tubular stem for detachable connection to said rotation means.

12. The oral hygiene system as recited in claim 11 wherein each of said heads have a front portion with a plurality of tuffs of bristles anchored therein, said front portion being arranged so that in one of said plurality of locations of said rotation means the bristles of the head are at about a 45 degree angle relative to the surface of the teeth and gums when said flat portion of said handle is generally parallel to the surface of the teeth whereby the Bass technique of brushing teeth and gums is implemented by the user of the oral hygiene system by moving the bristles in short strokes against the surface of the teeth in a conventional manner.

13. The oral hygiene system as recited in claim 12 wherein each of said stems comprises means for laterally adjusting the position of said stem relative to the longitudinal axis of said handle.

14. The oral hygiene system as recited in claim 11 further comprising an enclosed storage container having a plurality of apertures therein for ventilation and means for receiving said handle, said stems, and said dental floss holder.

15. The oral hygiene system as recited in claim 14 wherein said storage container is formed of a transparent material.

16. An oral hygiene system, comprising:

a generally cylindrical handle, having a top portion, a central portion, a bottom portion, a longitudinal axis, and a cross-section defined by a circular portion for supporting one or more fingers and a flat portion for supporting a thumb and fingertips, wherein said handle is formed of a deformable material which is slightly depressed when a gripping force is applied thereto, said circular portion and said flat portion having a plurality of raised sections attached thereto defining grips, and wherein said generally cylindrical handle is about one (1) inch in diameter;

rotation means attached to the top portion of said handle which may be selectively positioned at one of a plurality of locations about the longitudinal axis of said handle, wherein said rotation means comprises a rotating disk, wherein said rotation means may be selectively positioned in about 45 degree increments;

a plurality of stems which may be detachably connected to said rotation means, said stems comprising means for laterally adjusting the position of said stems relative to the longitudinal axis of said handle, wherein each of said stems having heads of different shapes and bristles arrangements connected thereto, and said stems comprise a bendable wire centrally located in said stems of a size and stiffness sufficient to maintain the head and stem configuration selected by the user while at the same time sustaining the forces applied to the head and stem during brushing;

a dental floss holder having a tubular stem for detachable connection to said rotation means; and a generally U-shaped dental floss holder attached to said tubular stem.

* * * * *